United States Patent [19]
diZerega et al.

[11] Patent Number: 5,629,294
[45] Date of Patent: May 13, 1997

[54] COMPOSITIONS AND METHODS FOR PREVENTING ADHESION FORMATION

[75] Inventors: Gere S. diZerega, Pasadena; Kathleen E. Rodgers, Long Beach, both of Calif.

[73] Assignee: University of Southern California, Los Angeles, Calif.

[21] Appl. No.: 178,482

[22] Filed: Jan. 6, 1994

Related U.S. Application Data

[63] Continuation of Ser. No. 789,231, Nov. 7, 1991, abandoned.

[51] Int. Cl.$^6$ .......................... A61K 38/00; A61K 38/02; C07K 5/00; C07K 7/00
[52] U.S. Cl. ........................... 514/18; 514/9; 514/15; 514/16; 514/17; 530/300; 530/327; 530/328; 530/329; 530/330
[58] Field of Search ..................... 514/15, 16, 17, 514/18, 9; 530/300, 331, 330, 329, 328, 327

[56] References Cited

U.S. PATENT DOCUMENTS

| | | | |
|---|---|---|---|
| 4,517,686 | 5/1985 | Ruoslahti et al. | 623/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 530/330 |
| 4,661,111 | 4/1987 | Ruoslahti et al. | 623/11 |
| 4,746,508 | 5/1988 | Carey et al. | 424/88 |
| 4,792,525 | 12/1988 | Ruoslahti et al. | 435/240.243 |
| 4,857,508 | 8/1989 | Adams et al. | 514/18 |
| 5,100,875 | 3/1992 | Marguerie de Rotrou | 514/18 |
| 5,169,833 | 12/1992 | Hansen, Jr. et al. | 514/17 |
| 5,352,664 | 10/1994 | Carney et al. | 514/13 |

FOREIGN PATENT DOCUMENTS

| | | |
|---|---|---|
| 0380370 | 8/1990 | European Pat. Off. ..... A61K 31/395 |
| 0422938A1 | 4/1991 | European Pat. Off. . |
| 0422937A1 | 4/1991 | European Pat. Off. . |

OTHER PUBLICATIONS

Ruoslahti et al, *Cell,* vol. 44, Feb. 28, 1986, pp. 517–518.
STN international, *Fastnotes,* c/o Chemical Abstracts Service pp. 1–2.
Jun et al., *Chemical Abstracts,* vol. 111, 1989, Nov. 20, No. 21, Abstract No: 192366c.
Aumailley et al, FEBS Letts, vol. 291, No. 1, Oct. 1991, pp. 50–54.
Experimental Cell Research, vol. 190, 1990, pp. 17–24, Katow et al.
Progress in Developmental Biology Part B, vol. 217B, 1986, pp. 235–238 Poole et al.
Basson et al., "Spatiotemporal Segregation of Endothelial Cell Integrin and Nonintegrin Extracellular Matrix–binding Proteins during Adhesion Events:", *J. Cell Biol.* 110:789–801 (Mar., 1990).
Nishimura et al., "Ibuprofen in the Prevention of Experimentally Induced Postoperative Adhesions", *Am. J. of Med.* 77:102–106 (1984).
Sipes et al., "RGD Supported Corneal Wound Healing", *J. of Cellular Biochem. Suppl.* 15F:184 (1991).

Krissansen et al., "Identification of a Novel Integrin β Subunit Expressed on /Cultured Monocytes (Macrophages)", *J. Biol. Chem.* 265:823–830 (1990).
Gresham et al., "A Novel Member of the Integrin Receptor Family Mediates Arg–Gly–Asp–simulated Neutrophil Phagocytosis", *J. Cell. Biol.* 108:1935–1943 (1989).
Brown, E.L. and Goodwin, J.L., "Fibronectin Receptors of Phagocytes: Characterization of the ARg–Gly–Asp Binding Proteins of Human Monocytes and Polymorphonuclear Leukocytes", *Journal of Experimental Medicine* 167:777–93 (1988).
Wright et al., "C3bi Receptor (Complement Type 3) Recognizes a Region of Complement Protein C3 Containing the Sequence Arg–Gly–Asp", *Proc. Nat'l Acad. Sci.* 84:1965–1968 (1987).
Ruggeri et al., "Inhibition of Platelet Function with Synthetic Peptides Designed to be High–affinity Antagonists of Fibrinogen Binding to Platelets", *Proceedings Natl. Acad. Sciences* 83:5708–5712 (1986).
Diamond et al., "Synergistic Effects of INTERCEED (TC7) and Heparin in Reducing Adhesion Formation in the Rabbit Uterine Horn Model", *Fertility and Sterility* 55:389 (1991).
Abe et al., "The Effect of Intraperitoneal Administration of Sodium Tolmetin–HNyaluronic Acid on the Postsurgical Cell Infiltration in vivo", *J. Surg. Res.* 49:322 (1990).
Rodgers et al., "Inhibition of Postsurgical Adhesions by Liposomes Containing Nonsteroidal Antiinflammatory Drugs", *Int. J. Fertil.* 35:40 (1990).
Hoeckel et al., "Prevention of Peritoneal Adhesions in the Rat With Sustained Intraperitoneal Dexamethasone Delivered by a Novel Therapeutic System", *Annales Chirurgiae et Gynaecologiae* 76:306–313 (1987).
Lewis, D.H., "Controlled Release of Bioactive Agents From Lactide/Blycolide Polymers", Jason & Langer (eds), *Biodegradable Polymers as Drug Delivery Systems,* pp. 1–41 (1990).
Ruoslahti, E., "Fibronectin and Its Receptors", *Ann. Rev. Biochem.* 57:375–413 (1988).
Ruoslahti, E., "Versatile Mechanisms of Cell Adhesion", *The Harvey Lectures,* Series 84, pp. 1–17 (1990).
Cadroy et al., "RGDV Peptide Selectively Inhibits Platelet–dependent Thrombus Formation in Vivo", *J. Clin. Invest.* 84:939–944 (1989).
Rodgers, K., "Nonsteroidal Anti–Inflammatory Drugs (NSAIDs) In the Treatment of Postsurgical Adhesion", *Progress in Clinical and Biological Research* 358:119–129 (1990).

*Primary Examiner*—Avis M. Davenport
*Attorney, Agent, or Firm*—Robbins, Berliner & Carson, LLP

[57] ABSTRACT

Compositions and methods for prevention of adhesion formation, whereby an effective amount of one or more adhesion preventing RGD-containing peptides is administered for a period of time sufficient to permit tissue repair. The RGD-containing peptide is further characterized in that it inhibits platelet aggregation and does not induce inflammation or trauma at the site of administration. The RGD-containing peptide is preferably administered in conjunction with a delivery vehicle (e.g., microcapsules, microspheres, liposomes, viscous instillates and absorbable mechanical barriers) useful for maintaining local concentrations of the peptide at an effective level.

15 Claims, No Drawings

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

Arg Gly Asp
1

( 2 ) INFORMATION FOR SEQ ID NO:2:

( i ) SEQUENCE CHARACTERISTICS:
 ( A ) LENGTH: 7 amino acids
 ( B ) TYPE: amino acid
 ( D ) TOPOLOGY: linear ( x i ) SEQUENCE DESCRIPTION: SEQ ID NO:2:

Gly Arg Gly Asp Ser Pro Cys
1               5

( 2 ) INFORMATION FOR SEQ ID NO:3:

( i ) SEQUENCE CHARACTERISTICS:
 ( A ) LENGTH: 7 amino acids
 ( B ) TYPE: amino acid
 ( D ) TOPOLOGY: linear ( x i ) SEQUENCE DESCRIPTION: SEQ ID NO:3:

Gly Arg Gly Asp Ser Pro Lys
1               5

( 2 ) INFORMATION FOR SEQ ID NO:4:

( i ) SEQUENCE CHARACTERISTICS:
 ( A ) LENGTH: 10 amino acids
 ( B ) TYPE: amino acid
 ( D ) TOPOLOGY: linear ( x i ) SEQUENCE DESCRIPTION: SEQ ID NO:4:

Gly Xaa Gly Asp Ser Pro Ala Ser Ser Lys
1               5                   10

( 2 ) INFORMATION FOR SEQ ID NO:5:

( i ) SEQUENCE CHARACTERISTICS:
 ( A ) LENGTH: 10 amino acids
 ( B ) TYPE: amino acid
 ( D ) TOPOLOGY: linear ( x i ) SEQUENCE DESCRIPTION: SEQ ID NO:5:

Arg Gly Asp Ser Pro Ala Ser Ser Lys Pro
1               5                   10

( 2 ) INFORMATION FOR SEQ ID NO:6:

( i ) SEQUENCE CHARACTERISTICS:
 ( A ) LENGTH: 6 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:6:

Gly Arg Gly Asp Ser Pro
1               5

( 2 ) INFORMATION FOR SEQ ID NO:7:

( i ) SEQUENCE CHARACTERISTICS:
  ( A ) LENGTH: 6 amino acids
  ( B ) TYPE: amino acid
  ( D ) TOPOLOGY: linear ( x i ) SEQUENCE DESCRIPTION: SEQ ID NO:7:

Gly Arg Gly Asp Thr Pro
1               5

( 2 ) INFORMATION FOR SEQ ID NO:8:

( i ) SEQUENCE CHARACTERISTICS:
  ( A ) LENGTH: 6 amino acids
  ( B ) TYPE: amino acid
  ( D ) TOPOLOGY: linear ( x i ) SEQUENCE DESCRIPTION: SEQ ID NO:8:

Gly Arg Gly Asp Xaa Pro
1               5

( 2 ) INFORMATION FOR SEQ ID NO:9:

( i ) SEQUENCE CHARACTERISTICS:
  ( A ) LENGTH: 6 amino acids
  ( B ) TYPE: amino acid
  ( D ) TOPOLOGY: linear ( x i ) SEQUENCE DESCRIPTION: SEQ ID NO:9:

Gly Arg Gly Asp Asn Pro
1               5

( 2 ) INFORMATION FOR SEQ ID NO:10:

( i ) SEQUENCE CHARACTERISTICS:
  ( A ) LENGTH: 6 amino acids
  ( B ) TYPE: amino acid
  ( D ) TOPOLOGY: linear ( x i ) SEQUENCE DESCRIPTION: SEQ ID NO:10:

Xaa Arg Gly Asp Ser Pro
1               5

( 2 ) INFORMATION FOR SEQ ID NO:11:

( i ) SEQUENCE CHARACTERISTICS:
  ( A ) LENGTH: 4 amino acids
  ( B ) TYPE: amino acid
  ( D ) TOPOLOGY: linear ( x i ) SEQUENCE DESCRIPTION: SEQ ID NO:11:

Arg Gly Asp Ser
1

( 2 ) INFORMATION FOR SEQ ID NO:12:

( i ) SEQUENCE CHARACTERISTICS:
  ( A ) LENGTH: 5 amino acids
  ( B ) TYPE: amino acid
  ( D ) TOPOLOGY: linear ( x i ) SEQUENCE DESCRIPTION: SEQ ID NO:12:

Gly Arg Gly Asp Ser
1               5

( 2 ) INFORMATION FOR SEQ ID NO:13:

( i ) SEQUENCE CHARACTERISTICS:
  ( A ) LENGTH: 9 amino acids (B) TYPE: amino acid
(D) TOPOLOGY: circular (xi) SEQUENCE DESCRIPTION: SEQ ID NO:13:

Gly Xaa Arg Gly Asp Ser Pro Cys Ala
1               5

COMPOSITIONS AND METHODS FOR PREVENTING ADHESION FORMATION

This is a continuation of Ser. No. 07/789,231 filed Nov. 7, 1991, now abandoned.

BACKGROUND OF THE INVENTION

The present invention relates to the medical arts. In particular, the present invention is directed to compositions and methods for use in preventing the formation of postoperative adhesions.

Adhesion formation, in particular following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction; in addition, adhesions are associated with chronic or recurrent pelvic pain and infertility in females.

The pathogenesis of adhesion formation is complex and not entirely understood. The first step is believed to involve excess fibrin deposition to form a scaffold. Organization of the fibrin scaffold by cellular elements, including fibroblasts and mesothelial cells, then follows.

Various approaches for the prevention of adhesion formation have been actively explored. In general, the treatments fall into three categories: prevention of fibrin deposition in the peritoneal exudate; reduction of local tissue inflammation; and removal of fibrin deposits.

Therapeutic attempts to prevent fibrin deposition include peritoneal lavages to dilute or wash away fibrinous exudate, surgical techniques to minimize tissue ischemia and introduction of barriers to limit apposition of healing serosal surfaces. Although the use of agents affecting coagulation of the fibrinous fluid has also been proposed, results obtained to date suggest that the use of procoagulants in areas of substantial bleeding may actually promote adhesion formation.

Physical barriers have been used in attempts to prevent adhesion formation by limiting tissue apposition during the critical period of peritoneal healing, thereby minimizing the development of fibrin matrix between tissue surfaces. Barrier agents which have been employed include both mechanical barriers and viscous solutions. Mixed results have been obtained using a barrier comprising a thin sheet of expanded polytetrafluoro-ethylene; in any event, such a membrane is less than ideal, as it must be sutured into place and is nonabsorbable. While an absorbable barrier (for example, a barrier made of oxidized regenerated cellulose) would be preferable, not all studies have demonstrated the efficacy of such barriers in preventing adhesions. Liquid barriers have also been considered for use in preventing adhesions; for example, chondroitin sulfate and carboxymethyl cellulose have both shown some promise in animal models. In addition, solutions of dextran 70 (molecular weight =70,000) have been the subject of a number of clinical studies. Not all clinical evaluations of 32% dextran 70 have found a therapeutic effect, however, and the clinical use of the solution is also associated with clinically important side effects.

Anti-inflammatory drugs have been evaluated for their effects on postoperative adhesion formation, as they may limit the release of fibrinous exudate in response to inflammation at the surgical site. Two general classes of these drugs were tested: corticosteroids and nonsteroidal anti-inflammatory drugs. The results of corticosteroid use in animal studies have generally not been encouraging, and clinical use of corticosteroids is limited by their other pharmacologic properties. While experimental evaluations of nonsteroidal anti-inflammatory drugs in postoperative adhesion formation show promise, clinical evaluations of these drugs for adhesion prevention is needed.

The third approach explored to date involves the removal of fibrin deposits. Although proteolytic enzymes (e.g., pepsin, trypsin and papain) should theoretically augment the local fibrinolytic system and limit adhesion formation, these enzymes are rapidly neutralized by peritoneal exudates rendering them virtually useless for adhesion prophylaxis. While various fibrinolytics (for example, fibrinolysin, streptokinase and urokinase) have been advocated, a potential complication to the clinical use of these enzymes in postoperative therapy is excessive bleeding resulting from their administration. Topical application of a recombinant tissue plasminogen activator (rt-PA) has been shown to reduce adhesion formation in a variety of animal models; further research is necessary to develop suitable delivery systems to provide drug to the surgical site and identify the postoperative time when adhesion prevention is feasible.

To date, no single therapeutic approach has proven universally effective in preventing formation of postoperative intraperitoneal adhesions. Therefore, there is a need for compositions and methods which may be used safely and effectively to prevent adhesion formation in a variety of different contexts.

It is an object of the present invention to provide compositions and methods for the minimization or prevention of post-surgical adhesion formation.

SUMMARY OF THE INVENTION

In accordance with one aspect of the present invention, there is provided a composition for the minimization or prevention of adhesion formation comprising at least one peptide containing the amino acid sequence Arg-Gly-Asp in a drug delivery system which maintains an effective concentration of the peptide at a site of potential adhesion formation. The peptide containing the requisite amino acid sequence is further characterized in that it inhibits platelet aggregation and does not induce inflammation or trauma at the site of administration. Pursuant to another aspect of the present invention, adhesion formation is minimized or prevented by administration of at least one peptide containing the amino acid sequence Arg-Gly-Asp at a site of potential adhesion formation for a period of time sufficient to permit substantial tissue repair (e.g., re-epithelialization or mesothelial repair) at the site.

DETAILED DESCRIPTION OF THE INVENTION

The inventive composition and method are useful in minimizing or preventing adhesion formation, the most common cause of which is prior surgery. The inventive composition and method have been shown to be particularly effective in preventing adhesion formation in the peritoneum following surgery. In addition, the present invention finds utility in other contexts, e.g., for cardiovascular, orthopedic, thoracic, ophthalmic, CNS and other uses, where prevention of the formation of adhesions is a significant concern. For the purposes of the following discussion, attention is directed primarily to description of compositions and methods useful in inhibiting peritoneal adhesion formation.

The present invention contemplates the use of at least one non-naturally-occurring peptide containing the amino acid sequence Arg-Gly-Asp (hereinafter referred to using the conventional single-letter amino acid symbols RGD). The tripeptide RGD per se is contemplated for use in accordance with the present invention, as are longer peptides containing the RGD sequence, at or near either end or internally. In general, any peptide containing the intact sequence RGD and meeting the other characteristics discussed hereinafter would be suitable for use in accordance with the present invention.

A particularly suitable class of peptides for use in accordance with the present invention comprises heretofore identified peptides corresponding to sequences of known, naturally-occurring proteins. The RGD sequence has been characterized as a site that promotes cellular attachment (cell recognition site) in fibronectin and other extracellular matrix and platelet adhesion proteins [see, e.g., Ruoslahti, E., "Fibronectin and Its Receptors," *Ann. Rev. Biochem.* 57:375 (1988)]. A class of glycoproteins has been identified as comprising the receptors in the cell recognition system for cell-extracellular matrix interaction. These proteins (collectively referred to as integrins) are characterized by the involvement of the RGD sequence in ligand recognition and appear to play a significant role in the assembly of the extracellular matrix [Ruoslahti, E., "Versatile Mechanisms of Cell Adhesion," *The Harvey Lectures*, Series 84, pp. 1–17 (1990)]. A significant number of peptide fragments corresponding to portions of the amino acid sequences of integrins (in particular, fragments derived from fibronectin) have been substantially characterized and would in general be especially useful in carrying out the present invention. In addition, particular peptide isolates from snake venom contain the requisite sequence.

Examples of such fragments corresponding to portions of the amino acid sequence of fibronectin are disclosed in U.S. Pat. No. 4,589,881 (Pierschbacher et al.), U.S. Pat. No. 4,578,079 (Ruoslahti et al.), U.S. Pat. No. 4,614,517 (Ruoslahti et al.), U.S. Pat. No. 4,661,111 (Ruoslahti et al.), and U.S. Pat. No. 4,792,525 (Ruoslahti et al.), the entire disclosures of which are hereby incorporated by reference. The peptides suitable for use in accordance with the present invention may readily be prepared using, e.g., conventional solid phase and solution addition methods of synthesis, as generally acknowledged in the aforementioned patents to Pierschbacher et al. and Ruoslahti et al. In addition, hybrid proteins with suitable properties combining the RGD-containing peptide with another protein may be employed in accordance with the present invention; such hybrid proteins may be suitably prepared using, e.g., recombinant DNA techniques well known to those of skill in the art. In addition to sequences comprising only the typical L-form of the amino acids, use may be made of sequences comprising one or more D-amino acids, homologs and/or other modified forms of amino acids. Indeed, while reference is made throughout to peptides herein, it is not strictly necessary that the compounds for use in accordance with the present invention comprise only sequences of amino acids in a form corresponding to fragments of naturally-occurring proteins. To the extent that a compound contains the requisite RGD sequence and meets the other criteria specified herein, modifications and substitutions in peptide structure currently known to those skilled in the art or which may hereinafter be developed are contemplated as within the scope of the present invention.

A number of peptides useful in accordance with the present invention are available commercially from Telios Pharmaceuticals, Inc., San Diego, Calif. and Sigma Chemical Co., Saint Louis, Mo. Exemplary peptides include the following (unless otherwise indicated, the L-form of the amino acid is contemplated): Arg-Gly-Asp [SEQ. ID NO: 1], Gly-Arg-Gly-Asp-Ser-Pro [SEQ ID NO: 6], Gly-Arg-Gly-Asp-Thr-Pro [SEQ ID NO: 6], Gly-Arg-Gly-Asp-D-Ser-Pro [SEQ ID NO: 8], Gly-Arg-Gly-Asp-Asn-Pro [SEQ ID NO: 9], n-methyl-Gly-Arg-Gly-Asp-Ser-Pro [SEQ ID NO: 10], Arg-Gly-Asp-Ser [SEQ ID NO: 11], Gly-Arg-Gly-Asp-Ser [SER ID NO: 12], Gly-Pen-Gly-Arg-Gly-Asp-Ser-Pro-Cys-Ala (cyclical) [SEQ ID NO: 13][Pierschbacher, M. D. and E. Ruoslahti, *J. Biol. Chem.* 262:17294 (1987)], Gly-Arg-Gly-Asp-Ser-Pro-Cys, [SEQ ID NO: 2] Gly-Arg-Gly-Asp-Ser-Pro-Lys, [SEQ ID NO: 3]Gly-D-Arg-Gly-Asp-Ser-Pro-Ala-Ser-Ser-Lys [SEQ ID NO: 4]and Arg-Gly-Asp-Ser-Pro-Ala-Ser-Ser-Lys-Pro [SEQ ID NO: 5].

In broad terms, the class of RGD-containing peptides from which the peptides suitable for use in accordance with the present invention may be selected comprises non-naturally occurring peptides including the amino acid sequence RGD. Thus, peptides from which those suitable for use in accordance with the present invention may be selected include, but are not limited to, the peptides of U.S. Pat. No. 4,792,525 including the amino acid sequence Arg-Gly-Asp-R, wherein R is Ser, Cys or Thr.

Peptides suitable for use in accordance with the present invention are characterized by utility in inhibiting platelet aggregation. This utility may be evaluated using a number of different procedures which are known to those working in the field. One procedure whereby platelet aggregation is measured uses washed platelets isolated from fresh human blood drawn into acid-citrate-dextrose by differential centrifugation and gel filtration. The platelets are resuspended into modified Tyrode's buffer containing 2% bovine serum albumin, pH 7.2. Aggregation can be measured using an aggregometer at 37° C. at a stirring rate of 1000 rpm. The reaction mixture consists of 400 µl buffer, 10 µl buffer of synthetic peptide, 10 µl $CaCl_2$ (1 mM final concentration), and one or more activators of platelet aggregation, such as, fibrinogen, ADP, epinephrine or collagen. Aggregation is quantitated by monitoring increase in light transmission through the platelet suspension [Ruggeri, et al., "Inhibition of platelet function with synthetic peptides designed to be high-affinity antagonists of fibrinogen binding to platelets," *Proceedings National Academy of Sciences* 83:5708–12 (1986)].

An additional requirement for a peptide suitable for use in accordance with the present invention is that it not induce chronic inflammation or trauma at the site of administration. In view of the apparent importance of inflammation in the process of adhesion formation, it is important that peptides be screened for their inflammatory propensities. For purposes of the present invention, chronic inflammation around the site of tissue repair is determined as evidenced by granuloma formation consisting of fused mononuclear phagocytes or multinucleate giant cells. In principle, any RGD-containing peptide which inhibits platelet aggregation but does not induce chronic inflammation at the site of administration would be useful in reduction or prevention of adhesion formation.

While the present invention is not bound to any particular theory, it is believed that RGD-containing peptides may inhibit adhesion formation through a variety of mechanisms. Based upon research to date, adhesion formation is believed to require the deposition of fibrin. Excess fibrin, if deposited and not removed, provides a scaffold for attachment and organization of incoming cells. Organization and epithelialization of this scaffold results in adhesion formation. The RGD-containing peptides may interfere with several aspects of adhesion formation.

In evaluations of compositions comprising RGD-containing peptides, no bleeding was observed in the experimental animals. Because platelet aggregation typically precedes and accelerates fibrin deposition, it could be speculated that inhibition of platelet aggregation resulted in the reduction of fibrin deposition. Had there been a complete inhibition of platelet aggregation, however, bleeding would have been expected. Moreover, fibrin deposition has been observed to occur even in the absence of platelet aggregation. For example, patients with Glanzmann's thrombasthenia (in which platelet cohesion is defective) have increased bleeding time and mucocutaneous bleeding, even though platelet count is normal. It is believed that this is due either to deficient GP IIb-IIIa (the protein on the surface of platelets that binds fibrinogen, collagen, von Wildebrand factor, etc. and mediates platelet aggregation), or to expression of a non-functional form of this protein. Interestingly, these patients also have impaired clot retraction. This indicates that clotting can occur without platelet aggregation. Therefore, the utility of RGD-containing peptides in preventing adhesion formation can not be explained solely on the basis of their utility in inhibiting platelet aggregation.

An additional activity of the RGD-containing peptides which may be implicated in their utility in prevention of adhesion formation is macrophage chemotaxis and phagocytosis. Macrophages are important in the prevention of adhesions in that they secrete fibrinolytic proteases and phagocytose tissue debris. The aforementioned U.S. Pat. Nos. 4,578,079 and 4,792,525 note that intact fibronectin has been shown to promote phagocytosis (an activity linked to the cell attachment activity) and is chemotactic to macrophages (an activity correlated to the presence of the cell attachment domain). The RGD sequence has been shown to be important in the enhancement of monocyte and PMN phagocytosis [Brown, E. J. and J. L. Goodwin, "Fibronectin receptors of phagocytes: characterization of the Arg-Gly-Asp binding proteins of human monocytes and polymorphonuclear leukocytes," *Journal of Experimental Medicine* 167:777–93 (1988); Gresham, H. D. et al., "A novel member of the integrin receptor family mediates Arg-Gly-Asp-stimulated neutrophil phagocytosis," *Journal of Cell Biology* 108:1935–43].

Nonetheless, the activity profile suggested in U.S. Pat. No. 4,578,079 and 4,792,525 would not adequately explain the utility of RGD-containing peptides in the prevention of adhesion formation. Intact ligands for integrins (such as collagen) have been shown to induce chronic inflammation and granuloma formation, and as a result would be expected to induce adhesion formation. Although it has been suggested (in, e.g., U.S. Pat. Nos. 4,578,079 and 4,792,525) that various RGD-containing peptides might have utility in promoting wound healing, the identified activities of RGD-containing peptides to date do not adequately explain why these peptides are useful in preventing or minimizing adhesion formation (which is, in essence, an activity properly characterized as the prevention of adverse healing). Therefore, it was unexpected that RGD-containing peptides described in the prior art as promoting cell attachment would be found to have utility in the prevention of adhesion formation (which involves, in particular, the prevention of cell attachment to the fibrin scaffold).

Pursuant to the method of the present invention, at least one RGD-containing peptide is maintained in an effective concentration at the site of potential adhesion formation for a period of time sufficient to permit substantial re-epithelialization. While the term of administration may vary depending upon a number of factors which would be readily appreciated by those skilled in the art, in general a period of about four to about ten days, preferably about five to about seven days, would be adequate to prevent or substantially minimize adhesion formation.

The concentration of RGD-containing peptide may be varied over a fairly broad range. The concentrations of RGD-containing peptides which can be administered would be limited by efficacy at the lower end and the complication of increased bleeding at the upper end. In the only known study of RGD-containing peptides administered systemically to selectively inhibit platelet-dependent thrombus formation in vivo in a baboon model, RGDV was given at a rate of 0.35, 0.68 or 1.31 μmol/min to achieve local plasma concentrations of 25, 50 and 100 μM, respectively [Cadroy, Y. et al., "RGDV Peptide Selectively Inhibits Platelet-dependent Thrombus Formation in Vivo," *J. Clin. Invest.* 84:939–944 (1989)]. These doses were chosen for use in the baboon model of Cadroy et al., because 100 μM was the concentration necessary to effectively abolish platelet aggregation in response to ADP and collagen. With the doses of RGDV given in the baboon model, there was a dose-dependent reduction in platelet accumulation associated with the administration of a collagen substrate and ADP. For purposes of preventing adhesion formation using the exemplary tripeptide RGD administered in Example 1 herein, a rate of only about 0.2 μmol/min in the peritoneal cavity of the rabbits was found effective. Other peptides of different structure and molecular weight would be employed in corresponding amounts to provide roughly equivalent concentrations of species containing the RGD sequence.

In general, an amount of RGD-containing peptide in the range of about $2\times10^{-4}$ to about 8 μM of the active agent per kg body weight per minute is administered for a time sufficient to achieve the desired effect or no more than about 7 days. The examples herein demonstrate that a total dose of between about 1.25 μg and about 2.4 mg per kg body weight is sufficient to achieve the therapeutic effect. For example, this dose in 50 ml of viscous instillate would correspond to a concentration in the range of about 2.5 g to about 4.8 mg/ml, and would deliver sufficient medicament to 100 kg of body weight.

The RGD-containing peptide may be administered directly in a suitable vehicle, for example phosphate-buffered saline (PBS). Although the present invention is not bound to any particular theory, it is speculated that a macrophage may phagocytose or otherwise cause the medicament to enter into or attach to the surface of a macrophage integrin (for example, MAC-1) [Wright, S. D. et al., "C3bi receptor (complement type 3) recognizes a region of complement protein C3 containing the sequence Arg-Gly-Asp," *Proc. Nat'l Acad. Sci.* 84:1965–1968 (1987); Krissansen, G. W. et al., "Identification of novel integrin β subunit expressed on cultured monocytes (macrophages). Evidence that one α subunit can associate with multiple β subunits," *J. Biol. Chem.* 265:823–830 (1990)]. Over a period of time, the peritoneal macrophage may discharge, release or otherwise cause the medicament to disperse at a later time. In this way, the medicament would be available to cause a therapeutic effect throughout the therapeutic interval. Another process by which the medicament administered in a suitable solution such as PBS would cause the therapeutic effect is by activating, altering or otherwise causing the macrophage itself to achieve the therapeutic effect.

Pursuant to preferred embodiments of the present invention, at least one RGD-containing peptide is administered in a drug-delivery system which enables the maintenance of requisite concentrations of the peptide for a period of time sufficient for re-epithelialization in a single dose delivery (for example, prior to suturing after surgery). While any suitable alternative would of course be contemplated as within the scope of the present invention, a number of drug-delivery systems would be particularly appropriate for administration of the RGD-containing peptide so as to maintain effective levels thereof over the requisite time period.

One suitable formulation to achieve the desired near zero-order release of the peptides comprises injectable microcapsules or microspheres prepared from a biodegradable polymer, such as poly(dl-lactide), poly(dl-lactide-co-glycolide), polycaprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 µm offer advantages over other delivery systems. For example, they generally use less active agent and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters such as crystallinity, molecular weight and composition. In particular, adjustment in the amount of drug released is generally achieved by modification of capsule wall thickness, capsule diameter, or both. Detailed information concerning the design, preparation and use of microspheres and microcapsules is provided by, e.g., Lewis, D. H., "Controlled Release of Bioactive Agents from Lactide/Glycolide Polymers," in Jason & Langer (eds.), *Biodegradable polymers as drug delivery systems*, pp. 1–41 (1990), the entire disclosure of which is hereby incorporated by reference. The sustained intraperitoneal release of dexamethasone using poly(lactide-co-glycolide) microparticles is described in Hoeckel, M. et al., "Prevention of Peritoneal Adhesions in the Rat with Sustained Intraperitoneal Dexamethasone Delivered by a Novel Therapeutic System," *Annales Chirurgiae et Gynaecologiae* 76:306–313 (1987), the entire disclosure of which is also incorporated by reference.

As is well known to those skilled in the art, various methods are currently available for preparing microcapsules, any of which could be employed to provide formulations in accordance with the present invention. Biodegradable polymeric materials suitable for preparation of microcapsules for controlled (i.e., near zero-order) release would be readily determined through routine experimentation by those skilled in the art. Moreover, alternative delivery systems suitable for use in accordance with the present invention (for example, fibers or filaments comprising the active agents) based on biodegradable polymers are also contemplated as within the scope of the present invention.

A further approach for the single-dose delivery of RGD-containing peptides in accordance with the present invention involves the use of liposomes. The encapsulation of an active agent in multilaminar vesicles (or liposomes) is a well known technique to assist in target drug delivery and prolong drug residence. In a typical procedure, a liposome-forming powdered lipid mixture is added to the desired quantity of active agent in aqueous solution (e.g., phosphate-buffered saline) to form a suspension. After a suitable hydration period, the hydrated suspension is then autoclaved to provide the liposome-active agent preparations. A lipid mixture suitable for formation of liposomes may be prepared from L-alpha-distearoyl phosphatidylcholine and cholesterol dissolved in chloroform, to which alpha-tocopherol is added; other compositions and methods for formation of liposomes would, however, also be useful for this purpose. The intraperitoneal administration of liposomes containing ibuprofen or tolmetin is described in Rodgers, K. et al., "Inhibition of Postsurgical Adhesions by Liposomes Containing Nonsteroidal Antiinflammatory Drugs," *Int. J. Fertil.* 35:40 (1990), the entire disclosure of which is hereby incorporated by reference.

Yet another suitable approach for single dose delivery of RGD-containing peptide involves the use of so-called viscous instillates. In this technique, high-molecular-weight carriers are used in admixture with the active agents, giving rise to an extended structure which produces a solution with high viscosity. Suitable high-molecular-weight carriers include dextran, carboxymethylcellulose and hyaluronic acid. While some studies have suggested that the use of viscous barrier solutions per se may have an advantageous effect in reducing the incidence of adhesion formation, it is believed that any such effect is of limited scope when compared to the combination of RGD-containing peptide and carrier. The intraperitoneal administration of a viscous instillate comprising tolmetin is described in Abe, H. et al., "The Effect of Intraperitoneal Administration of Sodium Tolmetin-Hyaluronic Acid on the Postsurgical Cell Infiltration In Vivo," *J Surg. Res.* 49:322 (1990), the entire disclosure of which is hereby incorporated by reference. Alternatively, the RGD-containing peptide could be directly attached to a chemical moiety which forms a viscous instillate (e.g., chondroitin sulfate), rather than simply admixed therewith [Sipes, N. J. et al., "RGD supported corneal wound healing," *Journal of Cellular Biochemistry Suppl.* 15F:184 (1991)].

In accordance with a particularly preferred embodiment of the present invention, at least one RGD-containing peptide is administered in combination with an absorbable mechanical barrier which alone reduces adhesion formation. As would be readily apparent to one working in the field, an RGD-containing peptide may be covalently or noncovalently (e.g., ionically) bound to such a barrier, or it may simply be dispersed therein. A particularly suitable mechanical barrier for use in this particular embodiment of the invention comprises oxidized regenerated cellulose; one such absorbable barrier is available under the designation INTERCEED(TC7) from Johnson and Johnson Medical, Inc., New Brunswick, N.J. The use of a mechanical barrier as a carrier to deliver heparin to traumatized surfaces is disclosed in Diamond, M. P. et al., "Synergistic effects of INTERCEED(TC7) and heparin in reducing adhesion formation in the rabbit uterine horn model," *Fertility and Sterility* 55:389 (1991), the entire disclosure of which is hereby incorporated by reference.

The invention may be better understood with reference to the accompanying example, which is intended to be illustrative only and should not be viewed as in any sense limiting the scope of the invention, which is defined hereinafter in the accompanying claims.

EXAMPLE

A study to confirm the efficacy of peptides containing the sequence arg-gly-asp in the reduction of adhesion formation after peritoneal surgery was performed. Rabbits underwent laparotomy followed by abrasion and devascularization of both uterine horns. This model was previously shown to cause severe adhesions in rabbits after surgery [Nishimura, K., Shimanuki, T. and diZerega, G. S., "The use of ibuprofen for the prevention of postoperative adhesions in rabbits," *Am. J. Meal.* 77:102–6 (1984)]. The peptide to be tested was placed in an Alzet miniosmotic pump to allow continuous release of the molecule throughout the postsurgical interval. The Alzet pump was placed in the subcutaneous space and a delivery tube connected the pump with the, site of delivery (uterine horns of the rabbit). Saline was placed in the pump of control rabbits. Two treatment groups were compared with this control group. One group was treated with the peptide Arg-Gly-Asp [SEQ ID NO: 1] at a concentration of 0.36 mg/ml (10 µl/hr delivery rate) and 0.6 mg was delivered over a 7 day postoperative period. The second group was treated with Arg-Gly-Asp-Ser-Pro-Ala-Ser-Ser-Lys-Pro [SEQ ID NO: 5] at a concentration of 0.22 mg/ml (10 µl/hr delivery rate) and 0.37 mg was delivered to each rabbit.

Seven days after surgery, the rabbits were sacrificed and the extent of adhesion formation involving the uterine horns was examined. Five rabbits in each group underwent surgery, but one from the control group and one from the group treated with Arg-Gly-Asp was eliminated due to infection or bleeding (or both). The data from this experiment was as follows:

| Treatment | Adhesion Score |
| --- | --- |
| Control (Saline) | 3.5+ |
|  | 3+ |
|  | 2+ |
|  | 3.5+ |
| Arg—Gly—Asp [SEQ ID NO: 1] | 2+ |
|  | 0.5+ |
|  | 2.5+ |
|  | 0.5+ |
| Arg—Gly—Asp—Ser—Pro—Ala— Ser—Ser—Lys—Pro [SEQ ID NO: 5] | 0.5+ |
|  | 0.5+ |
|  | 1.5+ |
|  | 1.5+ |
|  | 0.5+ |

The scoring range was from 0–4+ with 4+ indicating extensive adhesions; 0 indicating no adhesions. The lower the adhesion score, the less the extent of adhesion formation following surgery.

The ratings system used in the double uterine horn model was determined as follows:

| | |
| --- | --- |
| 0 | No adhesions; |
| 0.5 | Light, filmy pelvic adhesions involving only the bladder, typically only 1 or 2 small adhesions; |
| 1 | Light, filmy adhesions, not extensive although slightly more extensive than 0.5; |
| 1.5 | The adhesions are slightly more extensive and are tougher than a 1 rating. |
| 2 | Tougher adhesions, a little more extensive, one uterine horn has filmy adhesions and the other has adhesions between either the bowel or the bladder, but not both; |
| 2.5 | Same as 2, except that adhesions to the uterine horn are not filmy; |
| 3 | Tougher adhesions than 2, more extensive, both horns are attached to either the bladder or the bowel, some movement of the uterus possible; |
| 3.5 | Same as 3 but both horns attached to both bladder and bowel; |
| 4 | Severe adhesions, both horns attached to both bladder and bowel, unable to move uterus without tearing the adhesions. |

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

What is claimed:

1. A method for preventing adhesion formation, comprising:

Administering an effective amount of at least one RGD-containing peptide characterized by the sequence Arg-Gly-Asp-R, in which R is selected from the group consisting of Ser, Cys, Thr, Asn and d-Ser.

2. A method according to claim 1, wherein said tissue repair comprises re-epithelization.

3. A method according to claim 1, wherein said tissue repair comprises mesothelial repair.

4. A method according to claim 1, wherein the RGD-containing peptide is characterized by absence of chronic inflammation or trauma at a site of administration.

5. A method according to claim 4, wherein the RGD-containing peptide is further characterized by utility in inhibiting platelet aggregation.

6. A method according to claim 1, wherein the RGD-containing peptide has from three to about twenty amino acids.

7. A method according to claim 1, wherein the RGD-containing peptide is Arg-Gly-Asp.

8. A method according to claim 1, wherein the RGD-containing peptide is administered in the form of microcapsules or microspheres.

9. A method according to claim 8 wherein the microcapsules or microspheres comprise a biodegradable polymer selected from the group consisting of poly(dl-lactides), poly(dl-lactide-co-glycolides), polycaprolactones, polyglycolides, polylactic acid-co-glycolides, poly(hydroxybutyric acids), polyortho-esters, polyacetals and mixtures thereof.

10. A method according to claim 1, wherein the RGD-containing peptide is administered in the form of liposomes.

11. A method according to claim 10, wherein the liposomes comprise L-alpha-distearoyl phosphatidylcholine.

12. A method according to claim 1, wherein the RGD-containing peptide is administered in the form of an instillate.

13. A method according to claim 12, wherein the instillate comprises a high-molecular-weight carrier selected from the group consisting of dextran, carboxymethylcellulose, hyaluronic acid, chondroitin sulfate and mixtures thereof.

14. A method according to claim 1, wherein the RGD-containing peptide is administered in combination with an absorbable mechanical barrier.

15. A method according to claim 14, wherein the absorbable mechanical barrier comprises oxidized regenerated cellulose.

* * * * *